(12) United States Patent
Suyama

(10) Patent No.: US 9,505,094 B2
(45) Date of Patent: Nov. 29, 2016

(54) WORK HOLDING DEVICE AND CUTTING DEVICE

(71) Applicant: Roland DG Corporation, Hamamatsu-shi, Shizuoka (JP)

(72) Inventor: Akihiro Suyama, Hamamatsu (JP)

(73) Assignee: ROLAND DG CORPORATION, Shizuoka (JP)

( * ) Notice: Subject to any disclaimer, the term of this patent is extended or adjusted under 35 U.S.C. 154(b) by 67 days.

(21) Appl. No.: 14/568,325

(22) Filed: Dec. 12, 2014

(65) Prior Publication Data

US 2015/0174716 A1   Jun. 25, 2015

(30) Foreign Application Priority Data

Dec. 24, 2013  (JP) .................................. 2013-265656

(51) Int. Cl.
*B23C 1/14* (2006.01)
*B23Q 3/06* (2006.01)
(Continued)

(52) U.S. Cl.
CPC .............. *B23Q 3/06* (2013.01); *A61C 13/0004* (2013.01); *A61C 13/0022* (2013.01); *A61C 13/083* (2013.01); *A61C 13/12* (2013.01);
(Continued)

(58) Field of Classification Search
CPC .......... A61C 13/0004; A61C 13/0009; B23C 2226/18; Y10T 409/305656; Y10T 409/305824; Y10T 409/307504; Y10T 409/309576; B25B 1/18; B25B 1/2436; B25B 1/2442; B25B 5/04; B25B 5/067; B25B 5/082; B25B 11/02

USPC ............ 269/60, 55, 143, 249, 71, 47, 289 R
See application file for complete search history.

(56) References Cited

U.S. PATENT DOCUMENTS 1,318,688 A * 10/1919 Paschall ................... B23Q 1/48
269/60
(Continued)

FOREIGN PATENT DOCUMENTS

DE           4114724 A1 * 11/1992  .............. B23Q 1/48
EP        2 247 405 B1      5/2011
(Continued)

OTHER PUBLICATIONS

Machine translation, German patent publication DE 4114724, "Workholding fixture for machine—has four rotational and three translational axes in confined space", Ziska et al., Nov. 12, 1992.*

(Continued)

*Primary Examiner* — Daniel Howell
*Assistant Examiner* — Chwen-Wei Su
(74) *Attorney, Agent, or Firm* — Keating and Bennett, LLP

(57) ABSTRACT

A work holding device includes a substantially C-shaped first frame that includes a first end and a second end and is rotatable about a first center axis that is located therebetween, and a substantially C-shaped second frame that includes a third end located between the first end and the first center axis and a fourth end located between the second end and the first center axis, the second frame being rotatable about a second center axis that passes the third end and the second end and is perpendicular or substantially perpendicular to the first center axis. A groove into which an edge of a work is insertable is provided in the second frame.

13 Claims, 9 Drawing Sheets

(51) Int. Cl.
  *B23C 1/06* (2006.01)
  *A61C 13/083* (2006.01)
  *A61C 13/00* (2006.01)
  *A61C 13/12* (2006.01)
  *B23Q 1/54* (2006.01)
  *B25B 1/18* (2006.01)
  *B25B 1/24* (2006.01)

(52) U.S. Cl.
  CPC .............. *B23C 1/06* (2013.01); *B23Q 1/5406* (2013.01); *B23Q 3/062* (2013.01); *B23C 2226/18* (2013.01); *B23Q 2220/004* (2013.01); *B25B 1/18* (2013.01); *B25B 1/2436* (2013.01); *B25B 1/2442* (2013.01); *Y10T 409/305656* (2015.01); *Y10T 409/305824* (2015.01); *Y10T 409/307504* (2015.01); *Y10T 409/309016* (2015.01); *Y10T 409/309576* (2015.01)

(56) References Cited

U.S. PATENT DOCUMENTS

| | | | | |
|---|---|---|---|---|
| 2,830,632 | A * | 4/1958 | La Rouche | B25B 11/00 269/133 |
| 3,566,112 | A | 2/1971 | Luecke | |
| 5,524,510 | A | 6/1996 | Davies et al. | |
| 5,860,197 | A * | 1/1999 | Fox | B25B 1/103 24/455 |
| 2005/0017411 | A1 * | 1/2005 | Yang | B29C 67/0055 264/319 |
| 2008/0187406 | A1 * | 8/2008 | Kai | B23C 1/06 409/197 |
| 2010/0260569 | A1 * | 10/2010 | Ham | B23Q 1/5406 409/80 |
| 2011/0018184 | A1 | 1/2011 | Steger | |
| 2011/0104642 | A1 * | 5/2011 | Luksch | A61C 13/0004 433/201.1 |
| 2012/0266783 | A1 * | 10/2012 | Yoshida | B23Q 1/4857 108/2 |
| 2014/0033491 | A1 * | 2/2014 | Donaldson | B25B 11/02 29/237 |
| 2014/0035243 | A1 * | 2/2014 | Hoop | B25F 3/00 279/145 |

FOREIGN PATENT DOCUMENTS

| | | |
|---|---|---|
| FR | 1 575 196 A | 7/1969 |
| FR | 2 631 100 A1 | 11/1989 |
| GB | 2 293 994 A | 4/1996 |
| JP | 2008-47841 A | 2/2008 |
| JP | 2013169617 A * | 9/2013 |
| WO | 2009/100863 A2 | 8/2009 |

OTHER PUBLICATIONS

Machine translation, Japan patent publication, JP 2008047841, "Holder device", Suzuki et al., Feb. 2008.*
Official Communication issued in corresponding Japanese Patent Application No. 2013-265656, mailed on Nov. 10, 2015.
Official Communication issued in corresponding European Patent Application No. 14197630.8, mailed on May 6, 2015.

* cited by examiner

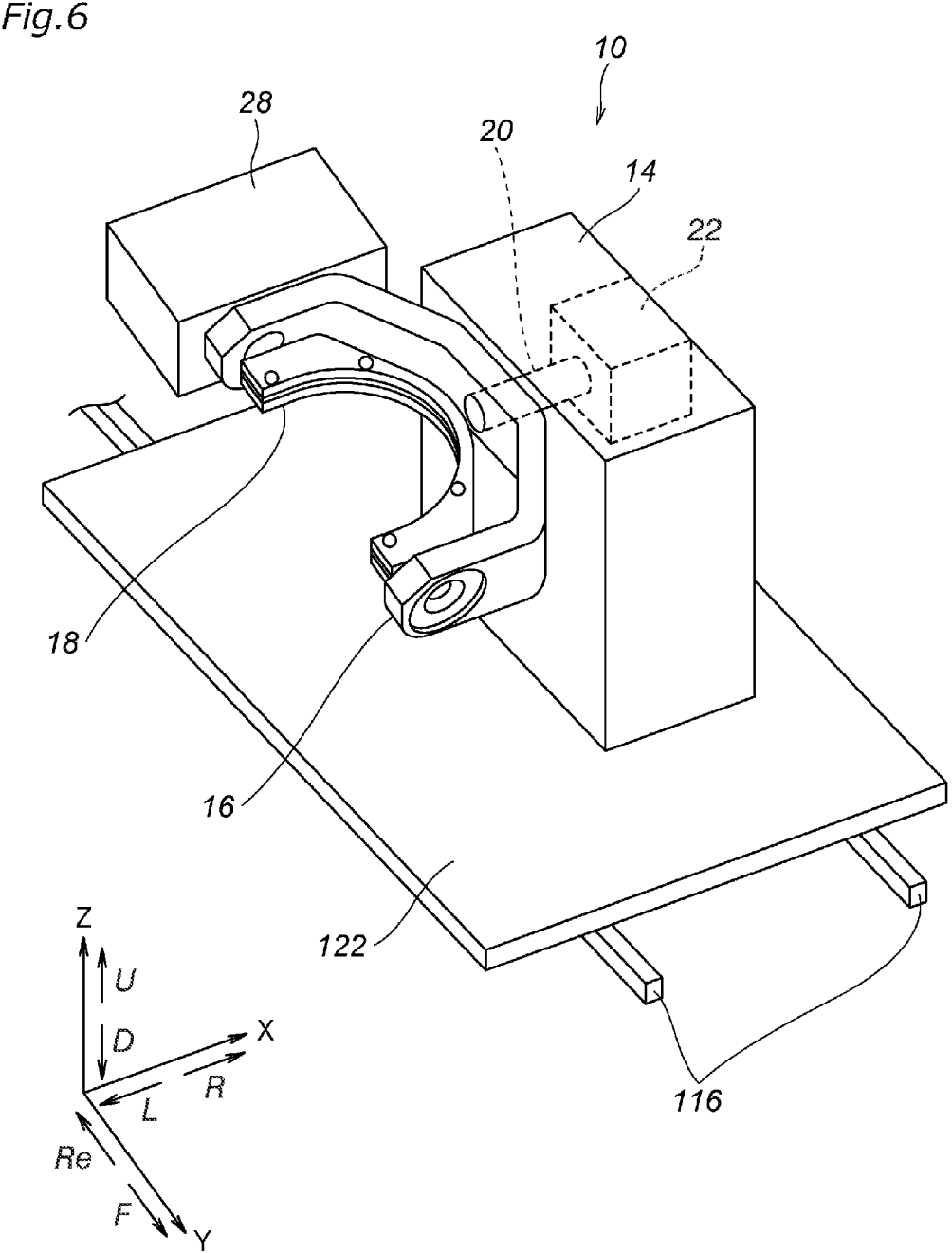

WORK HOLDING DEVICE AND CUTTING DEVICE

The present application claims priority from Japanese Patent Application No. 2013-265656 filed on Dec. 24, 2013, which is incorporated by reference herein in its entirety.

BACKGROUND OF THE INVENTION

1. Field of the Invention

The present invention relates to a work holding device that holds a work that is to be processed by a processing tool and a cutting device including such a work holding device.

2. Description of the Related Art

Conventionally, a cutting device that performs a cutting process on a work based on predetermined data by use of numerical value control performed by a microcomputer or the like is known. Such a cutting device includes a work holding device that holds the work. Such a cutting device and such a work holding device are disclosed in, for example, European Patent No. 2247405.

FIG. 7 is a perspective view of a conventional cutting device 300. The cutting device 300 includes a carriage 312 movable in an X-axis direction, a table 322 movable in a Y-axis direction, and a main shaft 314 movable in a Z-axis direction. A processing tool 332 is attached to the main shaft 314.

A work holding device 310 is located on the table 322. As shown in FIG. 8, the work holding device 310 includes a frame 328 that holds a discus-shaped work 200 (shown in FIG. 7) and a frame 326 that supports the frame 328. The frame 326 is rotatable about a center axis O1 that is parallel or substantially parallel to the X-axis. The frame 328 is rotatable about a center axis O2 that is parallel or substantially parallel to the Y-axis.

As shown in FIG. 9A and FIG. 9B, the frame 328 includes a base member 150 and a cap member 152. A thread 150a is formed in an outer circumferential surface of the base member 150, and a thread 152a engageable with the thread 150a is formed in an inner circumferential surface of the cap member 152. The cap member 152 is detachable from the base member 150.

The work 200 is caused to be held by the frame 328 as follows. The cap member 152 is detached from the base member 150 and is put outside the cutting device 300. Next, the work 200 is placed on the base member 150. Then, the cap member 152 is attached to the base member 150 and is rotated. As a result, the work member 200 is sandwiched between the cap member 152 and the base member 150 and thus is held by the frame 328.

The work 200 which has been processed is recovered from the frame 328 as follows. The cap member 152 is detached from the base member 150 and is put outside the cutting device 300. Next, the work 200 is removed from the base member 150.

As described above, with the work holding device 310, the cap member 152 needs to be put outside the cutting device 300 in order to cause the work 200 to be held by the frame 328 and also to be recovered from the frame 328. This involves an undesirable possibility that the cap member 152 is lost during the operation.

The frame 328 is located inwardly relative to the frame 326, which is substantially rectangular. When rotating the cap member 152, an operator's finger is likely to contact the frame 326. Because of this, the operation of detaching the cap member 152 from the base member 150 and the operation of attaching the cap member 152 to the base member 150 are difficult.

SUMMARY OF THE INVENTION

Preferred embodiments of the present invention provide a work holding device configured to allow a process of causing a work to be held (hereinafter, referred to as a "work holding process") and an operation of recovering the work (hereinafter, referred to as a "work recovery process") to be performed easily by an operator with no disturbance by a component thereof.

Preferred embodiments of the present invention also provide a work holding device configured to allow a work holding process and a work recovery process to be performed with no need to detach a component thereof.

Preferred embodiments of the present invention further provide a cutting device including such a work holding device.

A work holding device according to a preferred embodiment of the present invention is a work holding device that holds a work that is to be processed by a processing tool. The work holding device includes a substantially C-shaped first frame and a substantially C-shaped second frame. The first frame includes a first end and a second end. The first frame is rotatable as centered around a first center axis that is located between the first end and the second end. The second frame includes a third end located between the first end and the first center axis and a fourth end located between the second end and the first center axis. The second frame is rotatable as centered around a second center axis that passes the third end and the fourth end and is perpendicular or substantially perpendicular to the first center axis. A groove into which an edge of the work is insertable is provided in the second frame.

A cutting device according to a preferred embodiment of the present invention includes the above-described work holding device; and a cutting tool as the processing tool.

The above-described work holding device is configured to allow a work holding process and a work recovery process to be performed with no disturbance by any component thereof. The work holding device also is configured to allow the work holding process and the work recovery process to be performed with no need to detach any component thereof. The above-described cutting device includes such a work holding device.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 6 is a perspective view of a portion of a work holding device in another preferred embodiment according to the present invention.

DETAILED DESCRIPTION OF THE PREFERRED EMBODIMENTS

Figure 1:
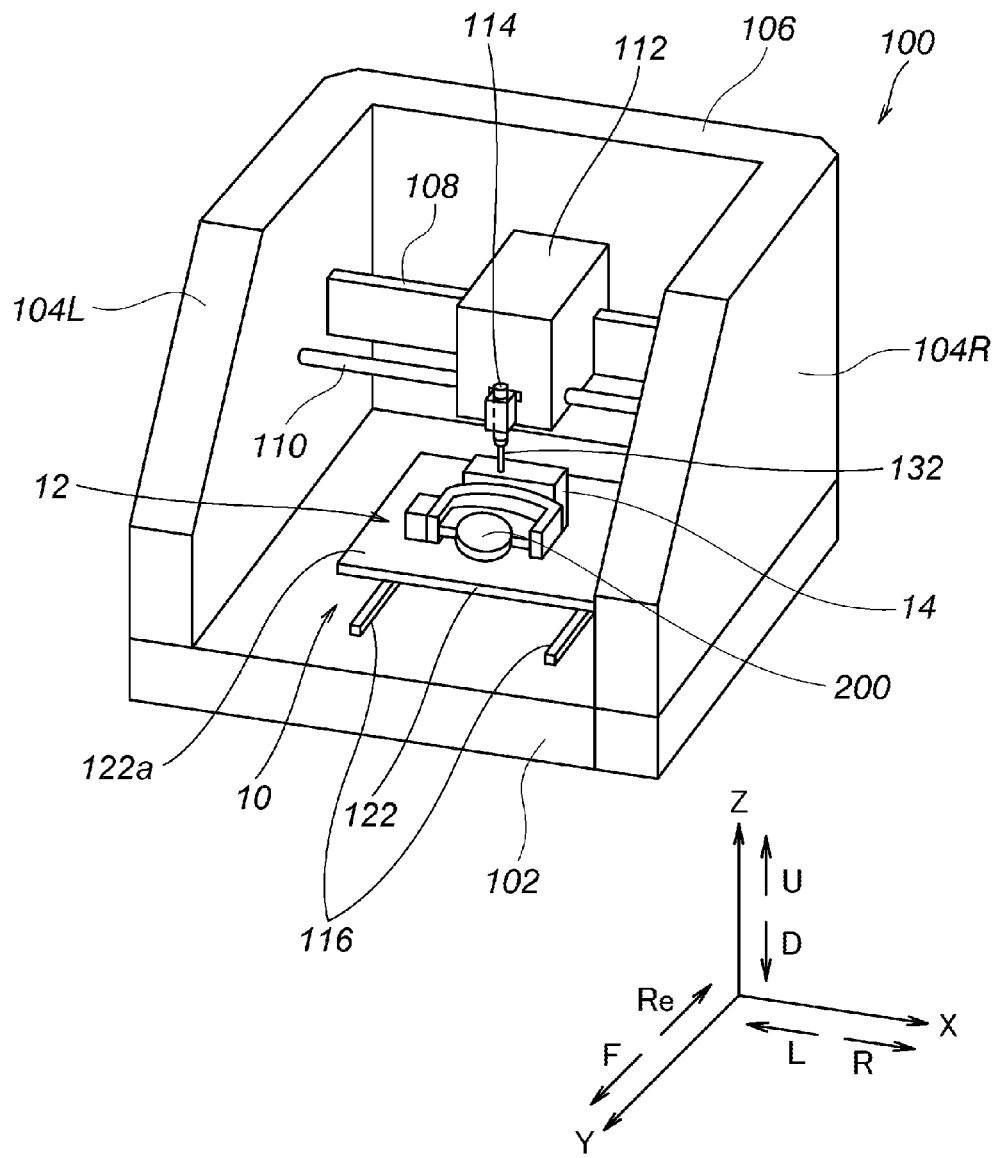
FIG. 1 is a perspective view of a cutting device according to a preferred embodiment according to the present invention.

Hereinafter, preferred embodiments of a work holding device and a cutting device according to the present invention will be described with reference to the attached drawings. As shown in FIG. 1, a work holding device 10 is included in a cutting device 100. First, a structure of the cutting device 100 will be described, and then a structure of the work holding device 10 will be described.

The cutting device 100 preferably includes a base member 102, a left wall 104L assembled to a left end of the base member 102, and a right wall 104R assembled to a right end of the base member 102. The left wall 104L and the right wall 104R are perpendicular or substantially perpendicular to the base member 102. A rear wall 106 is provided to the rear of the left wall 104L and the right wall 104R. The rear wall 106 couples the left wall 104L and the right wall 104R to each other. The left wall 104L, the rear wall 106 and the right wall 104R preferably are integrally formed in this preferred embodiment, but these walls may be separately formed.

The cutting device 100 includes a guide rail 108 and a shaft 110. A left end of the guide rail 108 is supported by the left wall 104L, and a right end of the guide rail 108 is supported by the right wall 104R. The guide rail 108 extends in an X-axis direction in an XYZ orthogonal coordinate system. Hereinafter, the directions up, down, left and right as seen from a person who is at a position in front of the cutting device 10 while facing the cutting device 100 will be respectively referred to as "up", "down", "left" and "right". The direction in which the person who is in front of the cutting device 100 is distanced from the cutting device 100 will be referred to as "forward", and the direction in which the person who is in front of the cutting device 100 approaches the cutting device 100 will be referred to as "rearward". In the figures, letters U, D, L, R, F and Re respectively represent up, down, left, right, front and rear. The shaft 110 is located parallel or substantially parallel to the guide rail 108. The shaft 110 extends in the X-axis direction. A left end of the shaft 100 is supported by the left wall 104L, and a right end of the shaft 110 is supported by the right wall 104R.

The cutting device 100 further includes a carriage 112, a main shaft 114, and the work holding device 10. The carriage 112 is slidably attached to the guide rail 108 and also to the shaft 110. The carriage 112 is supported by the guide rail 108 and the shaft 110 so as to be movable in the X-axis direction. A processing tool 132 is attached to the main shaft 114. The processing tool 132 preferably is a rod or other similar object, for example. In this preferred embodiment, the processing tool 132 is a cutting tool, for example. The main shaft 114 is supported by the carriage 112 so as to be movable in a Z-axis direction. The work holding device 10 is located on a table 122 that is movable in a Y-axis direction.

Although not shown in FIG. 1, the cutting device 100 includes a motor that moves the carriage 112 in the X-axis direction, a motor that moves the table 122 in the Y-axis direction, and a motor that moves the main shaft 114 in the Z-axis direction. The cutting device 100 also includes a control device (not shown) that is configured or programmed to control the motors, and the control device is a microcomputer, for example.

A pair of guide rails 116 are provided on the base member 102. The table 122 is slidably engaged with the guide rails 116. Along the sliding of the table 122 on the guide rails 116, the work holding device 10 is moved in the Y-axis direction. The work holding device 10 includes a rotatable member 12 that is rotatable while holding a discus-shaped work 200.

Figure 2:
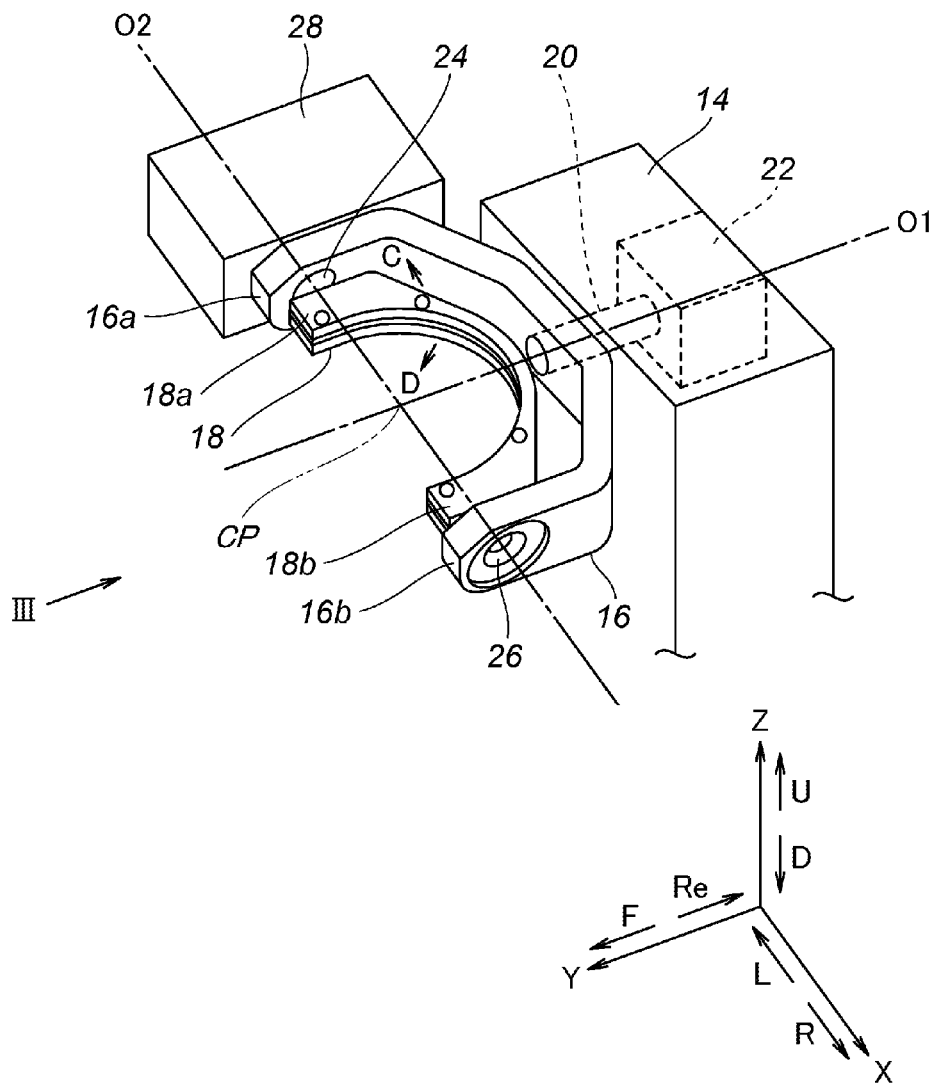
FIG. 2 is a perspective view of a portion of a work holding device according to a preferred embodiment according to the present invention.

A support member 14 is provided on the table 122. The support member 14 is secured to a top surface 122a of the table 122. As shown in FIG. 2, the rotatable member 12 includes a substantially C-shaped first frame 16 and a substantially C-shaped second frame 18. The first frame 16 is supported by the support member 14 so as to be rotatable about a first center axis O1 that is parallel or substantially parallel to the Y-axis. The second frame 18 is located inner to the first frame 16. The second frame 18 is structured to hold the work 200. The second frame 18 is supported by the first frame 16 so as to be rotatable about a second center axis O2 that is parallel or substantially parallel to the X-axis.

The shapes of the first frame 16 and the second frame 18 are not limited to those shown in FIG. 2. The first frame 16 and the second frame 18 may each have a curved shape having a constant curvature or a curved shape having a non-constant curvature. The first frame 16 and the second frame 18 may each include a straight portion. The first frame 16 and the second frame 18 are not each limited to having a curved shape and may have a shape that is bent with at least one pointed corner like a portion of a polygon (hereinafter, such a shape will be expressed as being "angled"). As shown in FIG. 2, the first frame 16 and the second frame 18 each include an inner edge and an outer edge. The inner edge defines an inner contour, and the outer edge defines an outer contour. Where an intersection of the first center axis O1 and the second center axis O2 is CP, the inner edge defines the contour closer to the intersection CP, and the outer edge defines the contour farther from the intersection CP. In this preferred embodiment, the inner edge and the outer edge of the first frame 16 preferably have the same shape. The inner edge of the second frame 18 is curved (more specifically, arc-shaped), and the outer edge of the second frame 18 is angled. The inner edge and the outer edge of the second frame 18 have different shapes. It should be noted that the inner edge and the outer edge of each of the first frame 16 and the second frame 18 may or may not have the same shape. There is no limitation on the length of the first frame 16 or the second frame 18. For example, in the case where the first frame 16 and the second frame 18 are both arc-shaped, the arc may be a semicircular arc (having a central angle of 180°) or may be longer than the semicircular arc (having a central angle larger than 180°) or shorter than the semicircular arc (having a central angle smaller than 180°).

In this specification, the shape represented by the term "substantially C-shaped" is not limited to an arc. In this preferred embodiment, since the work 200 is discus-shaped, the second frame 18 preferably has a shape of a semicircular arc. Alternatively, in the case where the work 200 is rectangular or substantially rectangular plate-shaped, the second frame 18 may be gate-shaped. "Gate-shaped" is encompassed in "substantially C-shaped". The shape of the second frame 18 may be appropriately set in accordance with the shape of the work 200. The shape of the first frame 16 may be appropriately set in accordance with the shape of the second frame 18.

A first motor 22 is located in the support member 14. The first motor 22 is controlled by the control section. The first motor 22 includes a first rotation shaft 20 extending forward. The first frame 16 is secured to a tip portion of the first rotation shaft 20. When the first motor 22 is driven, the first rotation shaft 20 is rotated. When the first rotation shaft 22 is rotated, the first frame 16 is rotated about the first center axis O1.

Figure 3:
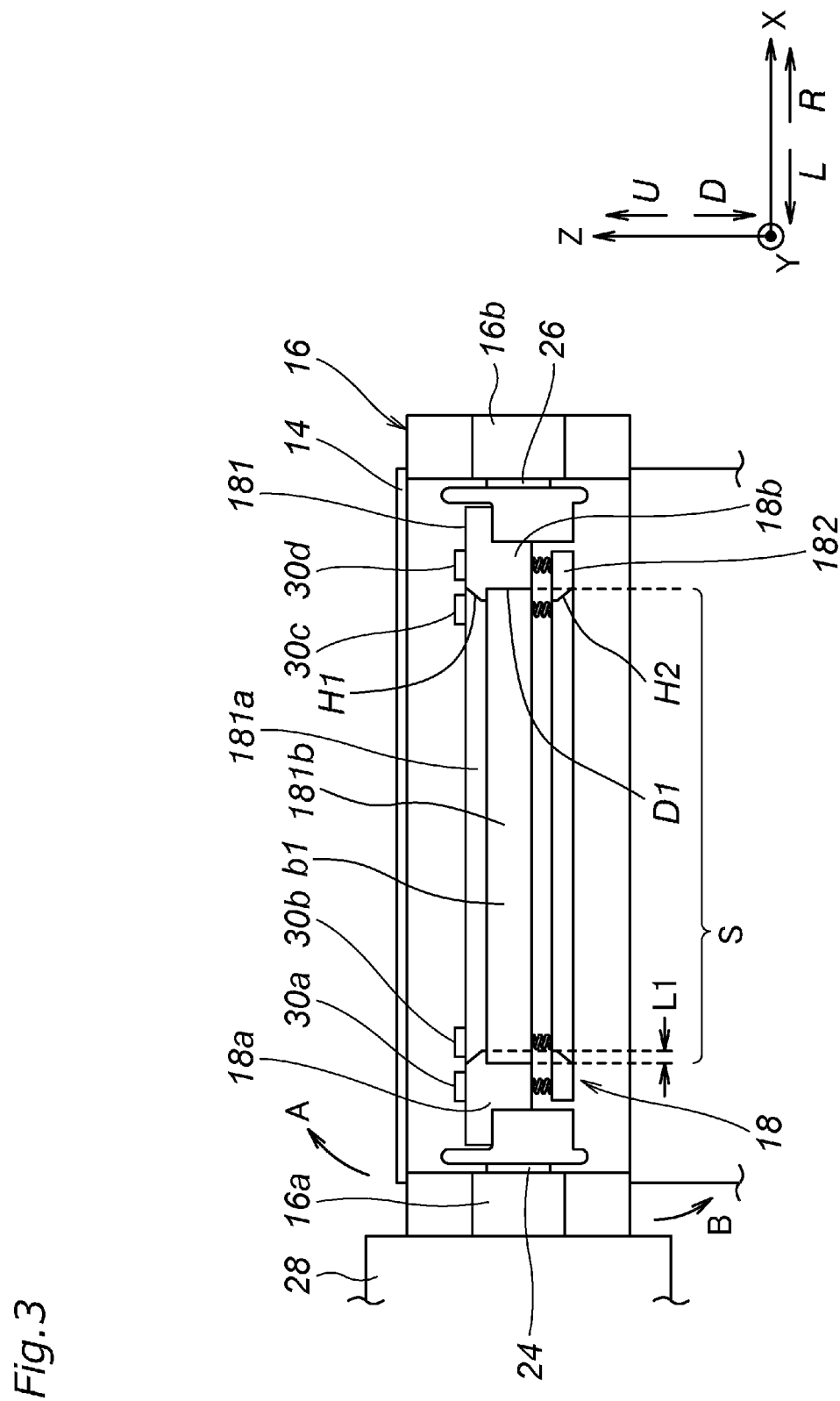
FIG. 3 is a view of the work holding device as seen in the direction of arrow III in FIG. 2.

There is no specific limitation on the range of rotation angles of the first frame 16. In this preferred embodiment, the first frame 16 preferably is rotatable between a position having an angle of −30° and a position having an angle of +30° from a horizontal position thereof, for example. A position having an angle of 0° is the position at which the first frame 16 is horizontal (i.e., the position at which the first frame 16 is parallel or substantially parallel to the X-Y plane as shown in FIG. 3). When the first frame 16 is rotated in the direction of arrow A in FIG. 3, the angle has a positive value, whereas when the first frame 16 is rotated in the direction of arrow B, the angle has a negative value.

The first frame 16 includes a first end 16a and a second end 16b. The first center axis O1 is between the first end 16a and the second end 16b. A second frame 18 includes a third end 18a and a fourth end 18b. The second center axis O2 passes the third end 18a and the fourth end 18b and is perpendicular or substantially perpendicular to the first center axis O1.

A second motor 28 is located to the left of the first frame 16. The second motor 28 is controlled by the control device. The second motor 28 includes a second rotation shaft 24. The second rotation shaft 24 extends along the second center axis O2. The second rotation shaft 24 passes throughout the first end 16a of the first frame 16 and is secured to the third end 18a of the second frame 18.

The first end 16a of the first frame 16 and the third end 18a of the second frame 18 are connected to each other via the second rotation shaft 24. The second rotation shaft 24 is rotatably supported by the first end 16a of the first frame 16, and is non-rotatably secured to the third end 18a of the second frame 18. The second end 16b of the first frame 16 and the fourth end 18b of the second frame 18 are connected to each other via a support shaft 26. The support shaft 26 is rotatably supported by the second end 16b of the first frame 16 and is non-rotatably secured to the fourth end 18b of the second frame 18. In this manner, the third end 18a is rotatably supported by the first end 16a via the second rotation shaft 24, and the fourth end 18b is rotatably supported by the second end 16b via the support shaft 26. The second frame 18 is rotatably supported by the first frame 16 via the second rotation shaft 24 and the support shaft 26. The support shaft 26 extends along the second center axis O2.

When the second motor 28 is driven, the second rotation shaft 24 is rotated about the second center axis O2. Along with the rotation of the second rotation shaft 24, the second frame 18 is rotated about the second center axis O2.

There is no specific limitation on the range of rotation angles of the second frame 18. In this preferred embodiment, the range of rotation angles of the second frame 18 preferably is set to −360° to +360°, for example. The second frame 18 is rotatable in the range of ±360° as centered around the second center axis O2. A position having an angle of 0° is the position at which the second frame 18 is horizontal (i.e., the position shown in FIG. 3). When the second frame 18 is rotated in the direction of arrow C in FIG. 2, the angle has a positive value, whereas when the second frame 18 is rotated in the direction of arrow D, the angle has a negative value.

As shown in FIG. 3, the second frame 18 includes a top member 181 and a bottom member 182. The top member 181 and the bottom member 182 are coupled to each other via four screws 30a, 30b, 30c and 30d. The bottom member 182 is configured to move upward or downward when the screws 30a, 30b, 30c and 30d are rotated by a tool. There is no specific limitation on the orientation of the screws 30a, 30b, 30c and 30d. In this preferred embodiment, the screws 30a, 30b, 30c and 30d are each located such that a head thereof is at a top end thereof when the second frame 18 is in a horizontal state and a holding area S (described later) is directed forward.

There is a gap between the top member 181 and the bottom member 182. The size of the gap is adjustable by rotating the screws 30a, 30b, 30c and 30d. It should be noted that the top member 181 and the bottom member 182 are structured such that the size of the gap does not exceed a certain size even by the rotation of the screws 30a, 30b, 30c and 30d. The bottom member 182 is structured so as not to be detached from the top member 181 even by the rotation of the screws 30a, 30b, 30c and 30d.

As shown in FIG. 3, the holding area S in which the work 200 is to be held is configured by the top member 181 and the bottom member 182. In this preferred embodiment, the holding area S preferably is set to hold approximately one half of a side circumferential surface 200a (see FIG. 4A) of the work 200, for example.

A portion 181b, of the top member 181, that defines the holding area S preferably has a substantially arc-shaped configuration having the same radius of curvature as that of the work 200. The top member 181 includes a flange portion 181a above the portion 181b. The flange portion 181a preferably has a substantially arc-shaped configuration having a radius of curvature smaller than that of the portion 181b. In other words, the flange portion 181a preferably has a substantially arc-shaped configuration having a radius of curvature smaller than that of the work 200. The bottom member 182 preferably has a substantially arc-shaped configuration having the same radius of curvature as that of the flange portion 181a of the top member 181.

The second frame 18 preferably has a substantially C-shaped vertical cross-section. In the vertical cross-section of the second frame 18, the flange portion 181a of the top member 181 and the bottom member 182 define a first protruding portion H1 and a second protruding portion H2 which protrude inward in a radial direction of the second frame 18. The portion 181b of the top member 181 defines a recessed portion D1 recessed outward in the radial direction. Between the first protruding portion H1 and the second protruding portion H2, a groove b1, into which an edge of the work 200 is insertable, is provided. The length from the recessed portion D1 to a tip of the first protruding portion H1 matches the length from the recessed portion D1 to a tip of the second protruding portion H2. The lengths are both L1. Alternatively, the lengths may be different from each other.

The work 200 is attached to the second frame 18 as follows. The first frame 16 and the second frame 18 are put into a horizontal state, and the holding area S of the second frame 18 is directed forward. Next, the four screws 30a, 30b, 30c and 30d are rotated to move the bottom member 182 downward. Namely, the bottom member 182 is located farther from the top member 181. Then, the work 200 is inserted toward the holding area S. Namely, the edge of the work 200 is inserted into the groove b1 defined by the top member 181 and the bottom member 182 (see FIG. 4A). Next, the screws 30a, 30b, 30c and 30d are rotated to move the bottom member 182 upward. Namely, the bottom member 182 is moved closer to the top member 181. As a result, the work 200 having a top surface and a bottom surface is sandwiched between the first protruding portion H1 and the second protruding portion H2 (see FIG. 4B). In this manner, the work 200 is held by the second frame 18.

This will be described more specifically. First, the first frame 16 and the second 18 are put into a horizontal state, and the holding area S of the second frame 18 is directed forward. Then, the screws 30a, 30b, 30c and 30d are rotated in a predetermined direction to move the bottom member 182 downward. As a result, the gap between the flange portion 181a of the top member 181 and the bottom member 182 is made larger. In other words, the gap between the first protruding portion H1 and the second protruding portion H2 in the vertical cross-section is made larger. Namely, the groove b1 is made wider. Next, the work 200 is inserted into the second frame 18 such that the side circumferential surface 200a of the work 200 contacts the recessed portion D1.

In the state where the work 200 is inserted into the second frame 18, the screws 30a, 30b, 30c and 30d are rotated in a direction opposite to the predetermined direction to move the bottom member 182 upward. As a result, the gap between the flange portion 181a of the top member 181 and the bottom member 182 is made smaller. In other words, the gap between the first protruding portion H1 and the second protruding portion H2 in the vertical cross-section is made smaller. Namely, the groove b1 is made narrower. As a result, the first protruding portion H1 is put into close contact with a top surface of the edge of the work 200, and the second protruding portion H2 is put into close contact with a bottom surface of the edge of the work 200. The work 200 is sandwiched between the first protruding portion H1 and the second protruding portion H2 (see FIG. 4B). Thus, the work 200 is held by the second frame 18.

For attaching the work 200 to the second frame 18, the table 122 may be located to a most forward position. In this case, the second frame 18 is located to the front of the carriage 112, the main shaft 114 and the like. Namely, none of the carriage 112, the shaft 114 and the like is above the second frame 18. In this state, the operation of rotating the screws 30a, 30b, 30c and 30d by use of a tool is performed easily.

With the work holding device 10, the work 200 is inserted into the second frame 18 from the front and then is sandwiched between the first protruding portion H1 and the second protrusion H2, and thus the work 200 is held. In this manner, the work 200 is held by the second frame 18 easily. The screws 30a, 30b, 30c and 30d are rotated and then the work 200 is pulled out of the second frame 18, so that the work 200 is detached from the second frame 18. In this manner, the work 200 is recovered easily.

Figure 5A:
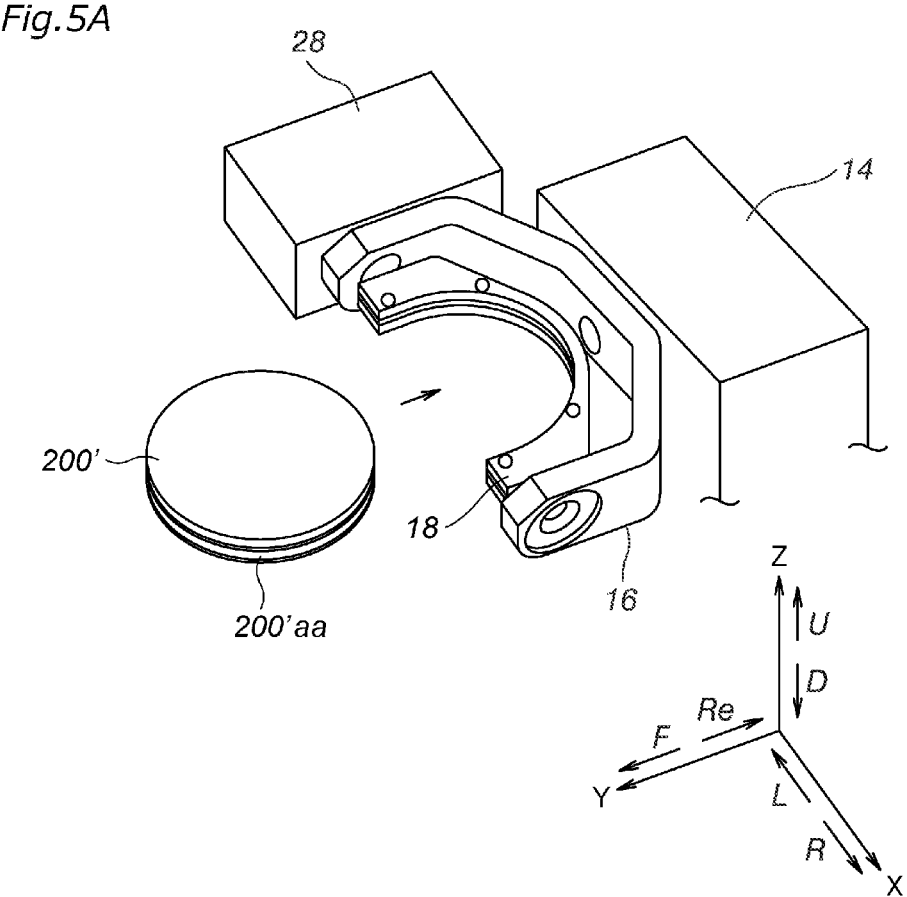
FIG. 5A shows how another work is inserted into the work holding device.
Figure 5B:
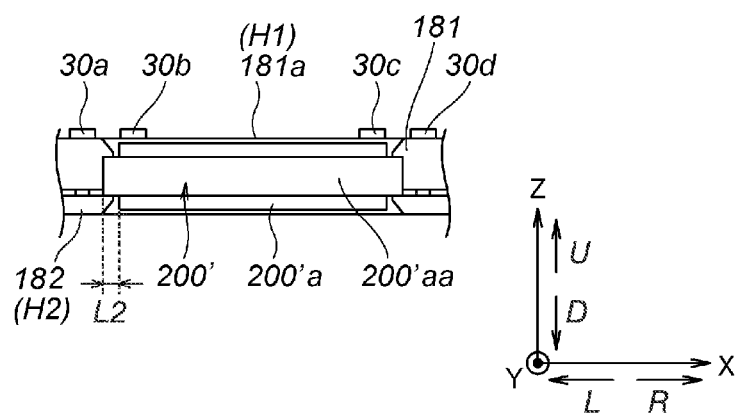
FIG. 5B is a front view of a portion of the work holding device having the another work inserted thereinto.
Figure 7:
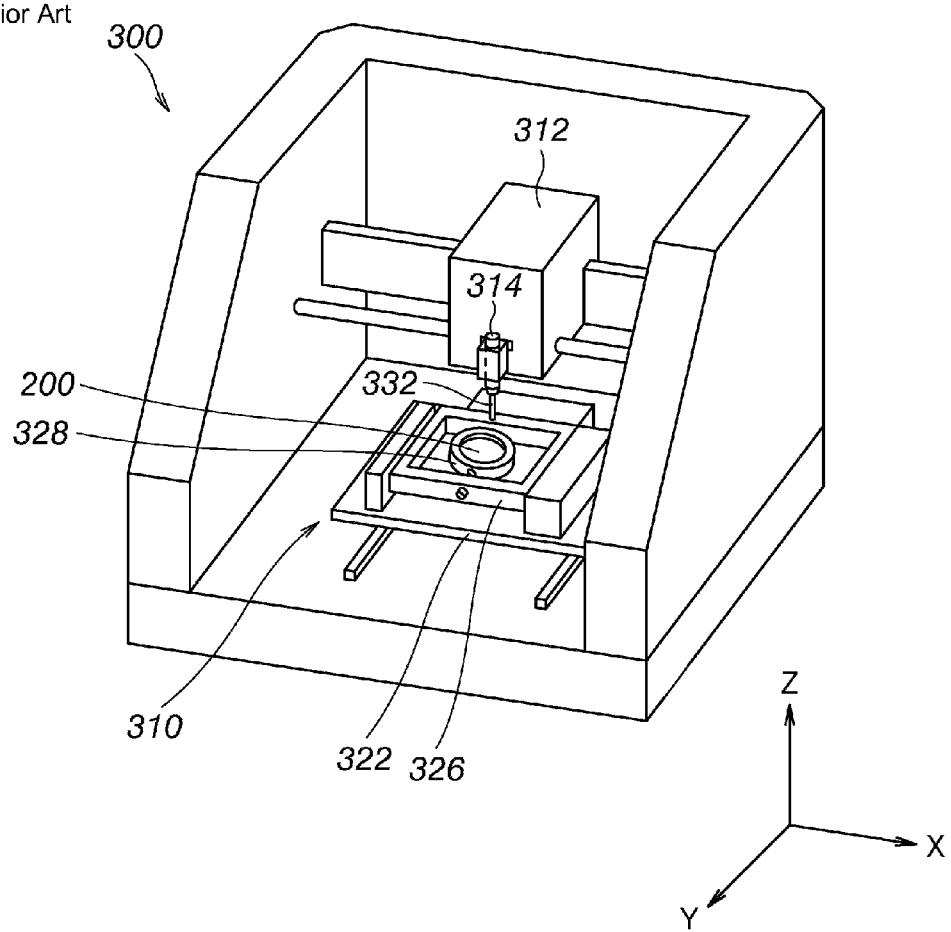
FIG. 7 is a perspective view of a cutting device including a conventional work holding device.
Figure 8:
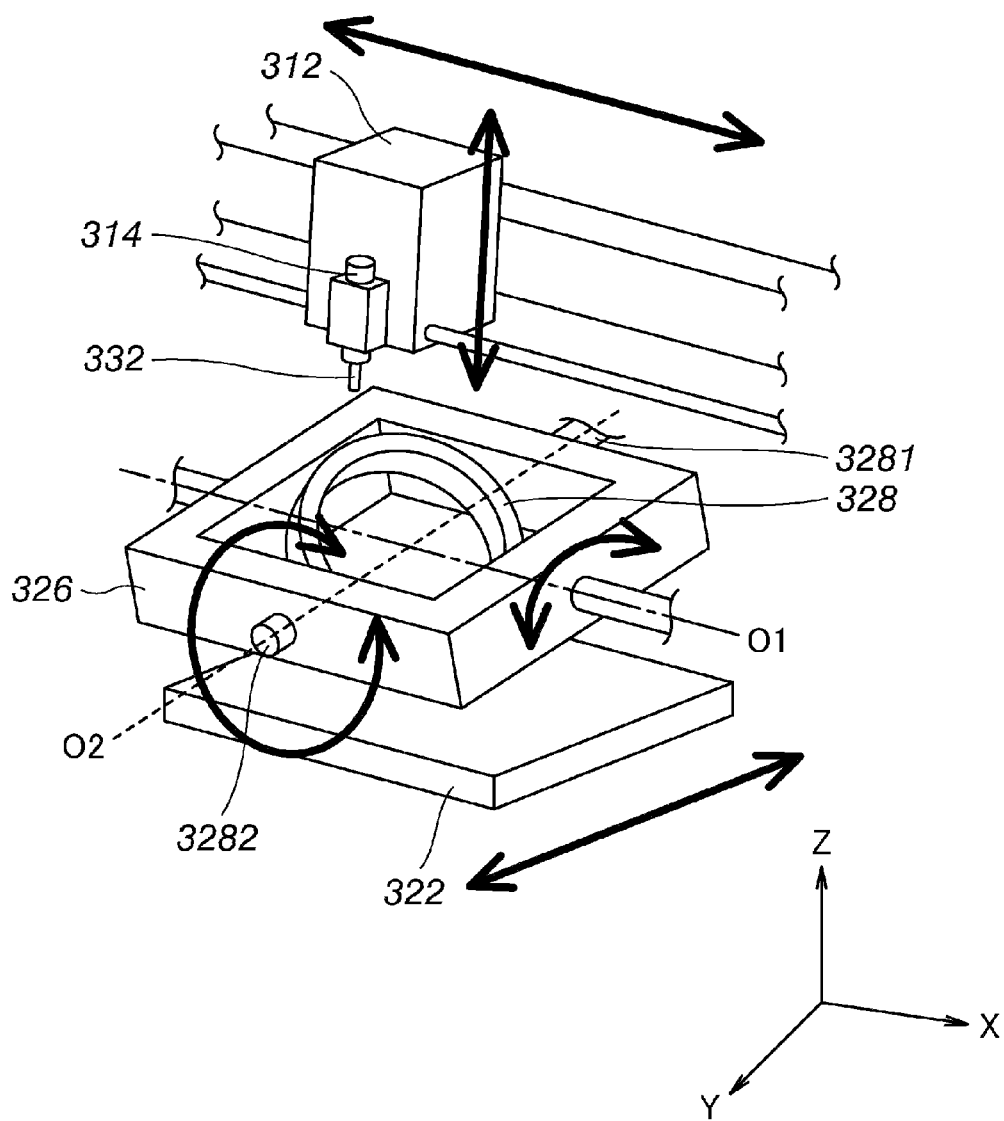
FIG. 8 is a perspective view of a portion of the conventional work holding device.
Figure 9A:
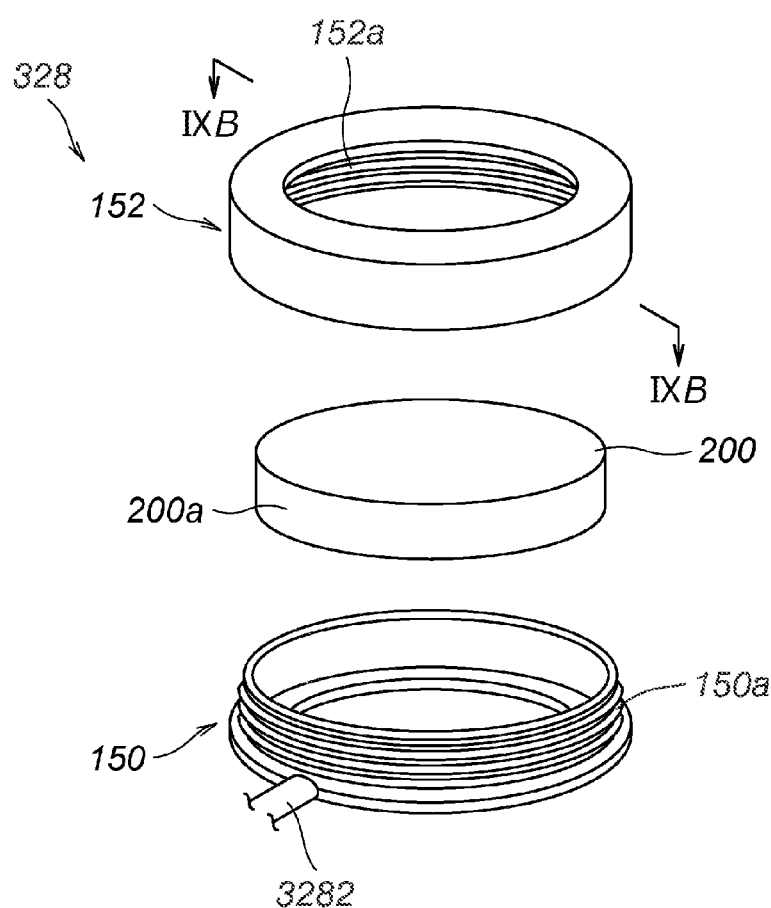
FIG. 9A is an exploded perspective view of a frame of the conventional work holding device.
Figure 9B:
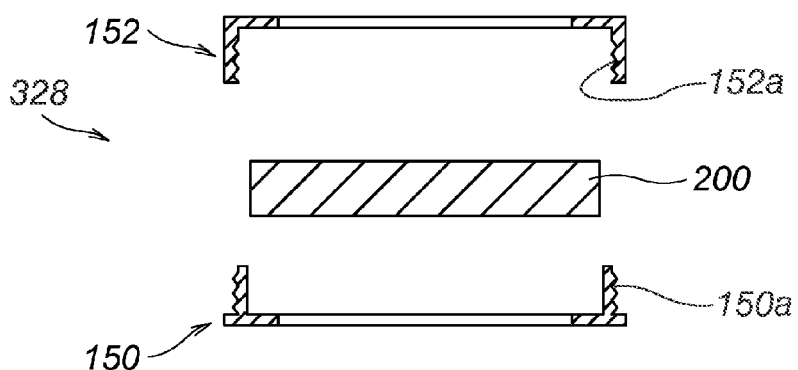
FIG. 9B is a cross-sectional view taken along line IXB-IXB in FIG. 9A.

There is no specific limitation on the shape of the work 200. For example, as shown in FIG. 5A and FIG. 5B, the work 200 may be modified to a work 200' including a protruding portion 200'aa on a side circumferential surface 200'a. The work 200' may be formed of, for example, a dental ceramic material or a dental wax material. For causing the work 200' to be held by the second frame 18, substantially the same operation as described above is performed so that the protruding portion 200'aa of the work 200' is sandwiched between the first protruding portion H1 and the second protruding portion H2. Length L1 from the recessed portion D1 to the tip of the first protruding portion H1, and/or length L1 from the recessed portion D1 to the tip of the second protruding portion H2, may be the same or substantially the same as length L2 from the protruding portion 200'aa of the work 200'.

The work holding device 10 allows the work 200', including the protruding portion 200'aa on the side circumferential surface 200'a, to be held by the second frame 18 easily, and also allows the work 200' to be detached from the second frame 18 easily, like in the case of the work 200.

The cutting device 100 performs a cutting process as follows. First, an operator attaches the processing tool 132 to the main shaft 114, and causes the work 200 to be held by the second frame 18 of the work holding device 10. The operation of causing the work 200 to be held by the second frame 18 is as described above. The operator inputs cutting data to the microcomputer (not shown).

Next, the operator operates an operation element (e.g., an operation button) of the cutting device 100 to instruct the start of the cutting process. When the start of the cutting process is instructed, the cutting device 100 appropriately moves the work holding device 10 in the Y-axis direction based on the input cutting data, appropriately moves the carriage 112 in the X-axis direction, and appropriately moves the main shaft 114 in the Z-axis direction. As a result, relative positions of the work 200 and the processing tool 132 in a three-dimensional space are appropriately changed.

The cutting device 100 drives the first motor 22 based on the input cutting data to appropriately rotate the first frame 16 about the first center axis O1, and drives the second motor 28 to appropriately rotate the second frame 18 about the second center axis O2. As a result, a relative posture of the processing tool 132 with respect to the work 200 is appropriately changed.

As a result, the processing tool 132 attached to the main shaft 114 is put into contact with any portion of the work 200 held by the second frame 18 at any angle. Therefore, the work 200 may be processed into a complicated shape.

As described above, the work holding device 10 does not have any component thereof disturb the operation of the work holding process or the work recovery process. Therefore, the work holding process or the work recovery process is performed easily. The work holding device 10 allows the work holding process or the work recovery process to be performed with no need to detach any component thereof. Therefore, there is no undesirable possibility that the component is lost during the work holding process or the work recovery process.

The work holding device 10 includes the first motor 22 including the first rotation shaft 20 that is secured to the first frame 16 and extends along the first center axis O1, and the second motor 28 including the second rotation shaft 24 that passes throughout the first end 16a of the first frame 16 and is secured to the third end 18a of the second frame 18. When the first motor 22 is driven, the first frame 16 is rotated about the first center axis O1. When the second motor 28 is driven, the second frame 18 is rotated about the second center axis O2. In this manner, the posture of the work 200 is freely changed.

In this preferred embodiment, the second rotation shaft 24 of the second motor 28 passes throughout the first end 16a of the first frame 16 and is secured to the third end 18a of the second frame 18. The second rotation shaft 24 is not limited to this. The second rotation shaft 24 of the second motor 28 may pass throughout the second end 16b of the first frame 16 and be secured to the fourth end 18b of the second frame 18. In this case, the third end 18a of the second frame 18 may be rotatably supported by the first end 16a of the first frame 16 via a support shaft.

In the work holding device 10, the second motor 28 is supported by the first frame 16. The second motor 28 is rotatable about the first center axis O1 together with the first frame 16. The work holding device 10 simplifies the mechanism of rotating the second frame 18 about the second center axis O2.

The second frame 18 includes the top member 181 as an example of a first member and the bottom member 182 as an example of a second member. The bottom member 182 is assembled with the top member 181 such that the groove b1 is provided between the top member 181 and the bottom member 182. The bottom member 182 is configured to be movable closer to, and farther from, the top member 181. When the bottom member 182 is moved farther from the top member 181, the grooved b1 is made wider. Therefore, the edge of the work 200 is inserted into the groove b1 easily. When the bottom member 182 is moved closer to the top member 181, the edge of the work 200 is sandwiched between the top member 181 and the bottom member 182. In this manner, the work 200 is held in a preferable manner. With the work holding device 10, the operation of causing the work 200 to be held by the second frame 18 is performed easily.

The work holding device 10 includes the screws 30a, 30b, 30c and 30d fit into the top member 181 and the bottom member 182. The bottom member 182 is in engagement with the screws 30a, 30b, 30c and 30d so as to be moved closer to, or farther from, the top member 181 by the rotation of the screws 30a, 30b, 30c and 30d. The work holding device 10 allows the bottom member 182 to be moved closer to, or farther from, the top member 181 easily by the rotation of the screws 30a, 30b, 30c and 30d.

In the vertical cross-section of the second frame 18, the top member 181 includes the first protruding portion H1 protruding inward in the radial direction, and the recessed portion D1 recessed outward in the radial direction. The recessed portion D1 is between the first protruding portion H1 and the bottom member 182. The bottom member 182 includes the second protruding portion H2 protruding inward in the radial direction. The groove b1 is provided between the first protruding portion H1 and the second protruding portion H2. The work holding device 10 allows the groove b1, into which the edge of the work 200 is insertable, to be defined by a simple structure.

In the work holding device 10, the second frame 18 has a shape of a semicircular arc. Owing to this, the discus-shaped work 200 is held in a preferable manner.

In the work holding device 10, at least one of the range of rotation angles of the first frame 16 about the first center axis O1 and the range of rotation angles of the second frame 18 about the second center axis O2 is larger than or equal to 360°. As a result, the top surface and also the bottom surface of the work 200 are easily processed.

The range of rotation angles of the second frame 18 about the second center axis O2 is larger than the range of rotation angles of the first frame 16 about the first center axis O1. The second frame 18 is located inner to the first frame 16, and thus is more easily rotatable than the first frame 16. Since the range of rotation angles of the second frame 18 is larger than the range of rotation angles of the first frame 16, the work 200 is processed easily or rapidly.

In this preferred embodiment, where the rotation angle of the first frame 16 when the first frame 16 is in a horizontal state is 0°, the range of rotation angles of the first frame 16 about the first center axis O1 preferably is −30° to +30°, for example. Where the rotation angle of the second frame 18 when the second frame 18 is in a horizontal state is 0°, the range of rotation angles of the second frame 18 about the second center axis O2 preferably is −360° to +360°, for example. As a result, the top surface and the bottom surface of the work 200 are processed easily or rapidly.

Figure 4A:
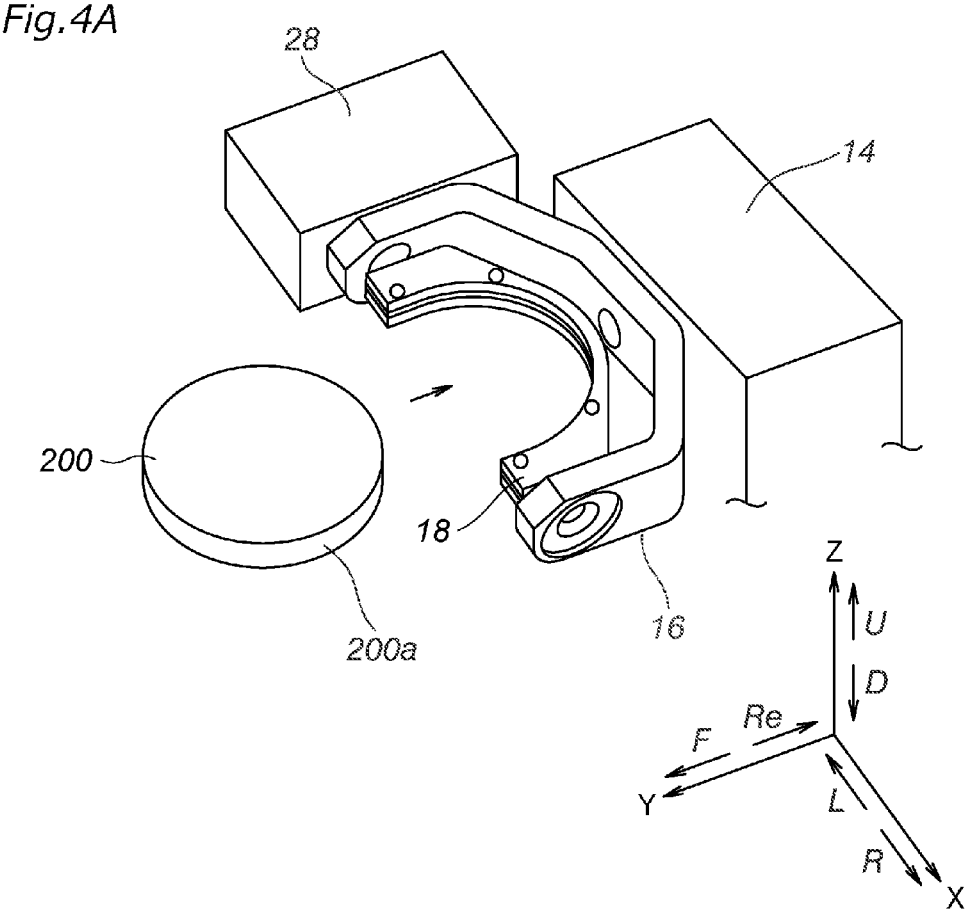
FIG. 4A shows how a work is inserted into the work holding device.
Figure 4B:
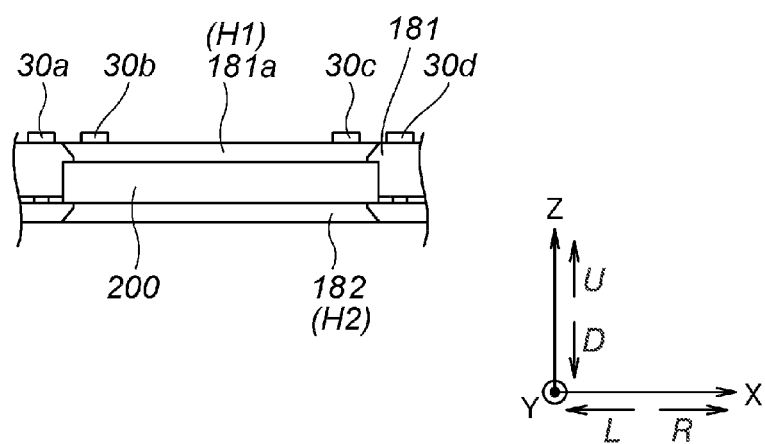
FIG. 4B is a front view of a portion of the work holding device having the work inserted thereinto.

In the work holding device 10, the first center axis O1 and the second center axis O2 extend horizontally. Therefore, as shown in FIG. 3 and FIG. 4A, the groove b1 is horizontal when the work 200 is to be inserted into the second frame 18. Thus, the work 200 is inserted into the second frame 18 in a horizontal state. Therefore, with the work holding device 10, the operation of causing the work 200 to be held is performed easily.

In the work holding device 10, the first center axis O1 extends forward and the second center axis O2 extends rightward. This allows the work 200 to be inserted into the second frame 18 from the front. Therefore, with the work holding device 10, the operation of causing the work 200 to be held is performed easily.

The cutting device 100 in this preferred embodiment includes the main shaft 114 that has the processing tool 132 configured to perform cutting attached thereto and is movable upward and downward, the carriage 112 that has the main shaft 114 attached thereto and is movable leftward and rightward, and the table 122 that is located below the processing tool 132 and is movable forward and rearward. The work holding device 10 is supported on the table 122. The cutting device 100 allows the position and the posture of the processing tool 132 with respect to the work 200 to be changed freely. The cutting device 100 is capable of processing the work 200 into a complicated shape.

The above-described preferred embodiment is merely an example. The present invention may be carried out in various other preferred embodiments as described below.

In the above-described preferred embodiment, the work holding device 10 preferably is movable in the Y-axis direction. The work holding device 10 is not limited to this. The work holding device 10 may be unmovably secured to the base member 102 while the processing tool 132 is movable in three directions of the X-axis direction, the Y-axis direction and the Z-axis direction. In the case where the work holding device 10 is movable in a direction other than the Y-axis direction, the moving direction of the carriage 112 and the moving direction of the processing tool 132 may be changed so that the relative positions of the work 200 held by the work holding device 10 and the processing tool 132 are changed in any way in a three-dimensional space. The work holding device 10 may be unmovable, or may be movable in any direction.

In the above-described preferred embodiment, the first frame 16 preferably is substantially C-shaped. The first frame 16 is not limited to this, needless to say. The first frame 16 may have any other shape that does not disturb the insertion of the work 200 toward the holding area S from the front in the state where the second frame 18 is horizontal and the holding area S of the second frame 18 is directed forward.

There is no limitation on the shape of the work 200. The work 200 may or may not be plate-shaped. For example, the work 200 may be block-shaped. The work 200 may have any shape having an edge that is insertable into the groove b1 of the second frame 18. There is no limitation on the material of the work 200. For example, the work 200 may be formed of a dental ceramic material like the work 200'. There is no limitation on the use of the cutting device 100. The cutting device 100 may be an artificial tooth production device that cuts a work formed of a dental ceramic material into a desired shape, or may be an artificial tooth production device that cuts a work formed of a resin material such as a dental wax material or the like into a desired shape.

In the above-described preferred embodiment, the range of rotation angles of the first frame 16 preferably is −30° to +30°, for example. The range of rotation angles of the first frame 16 is not limited to such a range, needless to say. The absolute value of a maximum possible rotation angle of the first frame 16 may be larger than 0° and smaller than 30°, or may be larger than 30° and smaller than or equal to 360°, for example. The absolute value of the maximum possible rotation angle of the first frame 16 may be, for example, 20° to 40°.

In the above-described preferred embodiment, the range of rotation angles of the second frame 18 preferably is −360 to +360°, for example. The range of rotation angles of the second frame 18 is not limited to such a range, needless to say. The absolute value of a maximum possible rotation angle of the second frame 18 may be larger than 0° and smaller than 360°, or may be larger than 360°, for example.

In the above-described preferred embodiment, as shown in FIG. 2, the first frame 16 is rotatable as centered around the first center axis O1 that is parallel or substantially parallel to the Y-axis. The first frame 16 is not limited to being movable in this manner, needless to say. For example, the first frame 16 may be rotatable as centered around a center axis that is parallel or substantially parallel to the X-axis. For example, as shown in FIG. 6, the first rotation shaft 20 of the first motor 22 may extend leftward so that the first frame 16 is secured to a left end of the first rotation shaft 20. In this case, in order to cause the work 200 to be held by the second frame 18, the first frame 16 and the second frame 18 are put into a horizontal state and the holding area S of the second frame 18 is directed leftward.

In the above-described preferred embodiment, the top member 181 and the bottom member 182 are connected to each other via the four screws 30a, 30b, 30c and 30d, for example. However, the top member 181 and the bottom member 182 are not limited to being connected in this manner. The number of the screws used to connect the top member 181 and the bottom member 182 may be one, two or three, or may be five or larger, for example. The top member 181 and the bottom member 182 may be connected to each other by any element other than the screw(s).

In the above-described preferred embodiment, the size of the gap between the top member 181 and the bottom member 182 is adjusted by the four screws 30a, 30b, 30c and 30d, for example. The gap is narrowed so that the work 200 is sandwiched between the top member 181 and the bottom member 182. The structure of holding the work 200 is not limited to this. Namely, any other structure by which the work 200 is sandwiched between the top member 181 and the bottom member 182 and thus is held by the second frame 18 is usable. The top member 181 and the bottom member 182 may each have any shape, and may be connected to each other by any mechanism.

In the above-described preferred embodiment, the bottom member 182 is not detachable from the top member 181. The bottom member 182 is not limited to this, needless to say. The bottom member 182 may be detachable from the top member 181.

The above-described preferred embodiments may be combined in any appropriate manner.

The terms and expressions used herein are for description only and are not to be interpreted in a limited sense. These terms and expressions should be recognized as not excluding any equivalents to the elements shown and described herein and as allowing any modification encompassed in the scope of the claims. The present invention may be embodied in many various forms. This disclosure should be regarded as merely describing preferred embodiments of the present invention. These preferred embodiments are provided with the understanding that they are not intended to limit the present invention to the preferred embodiments described in the specification and/or shown in the drawings. The present invention is not limited to the preferred embodiment described herein. The present invention encompasses any of preferred embodiments including equivalent elements, modifications, deletions, combinations, improvements and/or alterations which can be recognized by a person of ordinary skill in the art based on the disclosure. The elements of each claim should be interpreted broadly based on the terms used in the claim, and should not be limited to any of the preferred embodiments described in this specification or used during the prosecution of the present application.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A work holding device that holds a work that is to be processed by a processing tool, the work holding device comprising:
    a substantially C-shaped first frame including a first end and a second end and being rotatable about a first center axis located between the first end and the second end; and
    a substantially C-shaped second frame that includes a third end located between the first end and the first center axis, a fourth end located between the second end and the first center axis, and a substantially C-shaped inner surface located between the third end and the fourth end, the second frame being rotatable about a second center axis that passes the third end and the fourth end and is perpendicular or substantially perpendicular to the first center axis; wherein
    a substantially C-shaped groove configured to receive a portion of the work is provided in the inner surface of the second frame.

2. A work holding device according to claim 1, further comprising:
    a first motor including a first rotation shaft that is secured to the first frame and extends along the first center axis; and
    a second motor including a second rotation shaft that passes through the first end of the first frame and is secured to the third end of the second frame or that passes through the second end of the first frame and is secured to the fourth end of the second frame.

3. A work holding device according to claim 2, wherein the second motor is supported by the first frame.

4. A work holding device according to claim 1, wherein the second frame includes a first member and a second member assembled to the first member such that the groove is provided between the first member and the second member; and the second member is movable closer to, or farther from, the first member.

5. A work holding device according to claim 4, further comprising a screw fit into the first member and the second member; wherein
the second member is in engagement with the screw so as to be moved closer to, or farther from, the first member when the screw is rotated.

6. A work holding device according to claim 4, wherein
the first member includes a first protruding portion that protrudes inward in a radial direction of the second frame in a vertical cross-section of the second frame and a recessed portion that is recessed outward in the radial direction between the first protruding portion and the second member in the vertical cross-section of the second frame, and the second member includes a second protruding portion that protrudes inward in the radial direction in the vertical cross-section of the second frame; and
the groove is provided between the first protruding portion and the second protruding portion.

7. A work holding device according to claim 1, wherein the second frame has a shape of a semicircular arc.

8. A work holding device according to claim 1, wherein at least one of a range of rotation angles of the first frame about the first center axis and a range of rotation angles of the second frame about the second center axis is larger than or equal to 360°.

9. A work holding device according to claim 1, wherein a range of rotation angles of the second frame about the second center axis is larger than a range of rotation angles of the first frame about the first center axis.

10. A work holding device according to claim 9, wherein
the range of rotation angles of the first frame about the first center axis is −30° to +30° where the rotation angle of the first frame when the first frame is in a horizontal state is 0°; and
the range of rotation angles of the second frame about the second center axis is −360° to +360° where the rotation angle of the second frame when the second frame is in a horizontal state is 0°.

11. A cutting device, comprising:
the work holding device according to claim 1; and
a cutting tool defining the processing tool.

12. A cutting device according to claim 11, further comprising:
a main shaft that has the cutting tool attached thereto and is movable upward and downward;
a carriage that has the main shaft attached thereto and is movable leftward and rightward; and
a table that is located below the cutting tool and is movable forward and rearward; wherein
the work holding device is supported on the table.

13. A cutting device according to claim 11, wherein the work includes a dental ceramic material or a dental wax material, and the cutting device is an artificial tooth production device.

* * * * *